US00PP22812P2

(12) United States Plant Patent
Lindsey

(10) Patent No.: US PP22,812 P2
(45) Date of Patent: Jun. 26, 2012

(54) ***TAXODIUM* TREE NAMED 'SKYWARD'**

(50) Latin Name: *Taxodium distichum*
Varietal Denomination: Skyward

(76) Inventor: Robert M. Lindsey, Mustang, OK (US)

( * ) Notice: Subject to any disclaimer, the term of this patent is extended or adjusted under 35 U.S.C. 154(b) by 25 days.

(21) Appl. No.: 12/925,914

(22) Filed: Nov. 2, 2010

(51) Int. Cl.
*A01H 7/00* (2006.01)

(52) U.S. Cl. ..... Plt./213

(58) Field of Classification Search ..... Plt./213
See application file for complete search history.

*Primary Examiner* — June Hwu
(74) *Attorney, Agent, or Firm* — Penny J. Aguirre

(57) ABSTRACT

A new cultivar of *Taxodium distichum* named 'Skyward' characterized by its upright and tight growth habit with ascending branching and a rounded tip, its dense branching with a lush and full canopy of foliage from near the base to the top of the tree, its compact plant habit with a small and narrow profile reaching about 7 m in height and 1.2 m in width in 20 years, its lack of surface roots when grown in areas with moist soil, its observed resistance to disease, drought, and insect damage and its tolerance to heavy accumulations of ice.

3 Drawing Sheets

Botanical classification: *Taxodium distichum.*
Varietal denomination: 'Skyward'.

BACKGROUND OF THE INVENTION

The present invention relates to a new and distinct cultivar of *Taxodium distichum* and will be referred to hereafter by its cultivar name, 'Skyward'. 'Skyward' represents a new western bald cypress tree grown for landscape use.

The inventor discovered this new *Taxodium* as a whole plant mutation in winter of 1990 in the Inventor's tree farm that had been planted with seedlings of *Taxodium distichum* in Mustang, Okla. The original tree of 'Skyward' was observed on the tree farm for five years and then subsequently planted in the Inventor's personal garden in 1995 for further evaluation.

Asexual reproduction of the new cultivar was first accomplished by hardwood cuttings under the direction of the Inventor in Boring, Oreg. in December of 2008. Propagation by hardwood cutting, budding and grafting has shown that the characteristics of this cultivar are stable and are reproduced true to type in successive generations.

SUMMARY OF THE INVENTION

The following traits have been repeatedly observed and represent the characteristics of a 20 year-old tree the new cultivar. These attributes in combination distinguish 'Skyward', as unique from all other selections and forms of *Taxodium distichum* known to the Inventor.

1. 'Skyward' exhibits an upright and tight growth habit with ascending branching and a rounded tip.
2. 'Skyward' exhibits dense branching with a lush and full canopy of foliage from near the base to the top of the tree.
3. 'Skyward' exhibits a compact plant habit with a small and narrow profile, reaching about 7 m (23 feet) in height and 1.2 m (4 feet) in width in 20 years.
4. 'Skyward' has not been observed to produce surface roots when grown in areas with moist soil.

5. 'Skyward' has been observed to be resistant to disease, drought, and insect damage.
6. 'Skyward' has been observed to be tolerant to heavy accumulations of ice.

Typical plants of *Taxodium distichum* differ from 'Skyward' in having a pyramidal growth habit with lateral branching (less upward), a more open and less dense canopy, in being wider and taller in size, and in commonly developing surface roots and knees when grown in moist soils. 'Skyward' can be most closely compared to cultivars of *Taxodium distichum* that also exhibit a more narrow plant habit in comparison to the species, 'Michelson' (U.S. Plant Pat. No. 3,551) and 'Peve Minaret' (not patented). 'Michelson' differs in having a pyramidal plant habit, in being broader in width and taller in height, in having young stems that are redder in color, and in having a more vigorous growth habit. 'Peve Minaret' differs from 'Skyward' in having a more loosely arranged branching habit with a candelabra-like form, in being shorter in height and broader in width.

BRIEF DESCRIPTION OF THE DRAWING

The plant and plant parts depicted in the accompanied photographs illustrate the characteristics of a 20 year-old tree of 'Skyward' as grown in Mustang, Okla.

The photograph in FIG. 1 provides an overall view of the plant habit of 'Skyward'.

Figure 1:
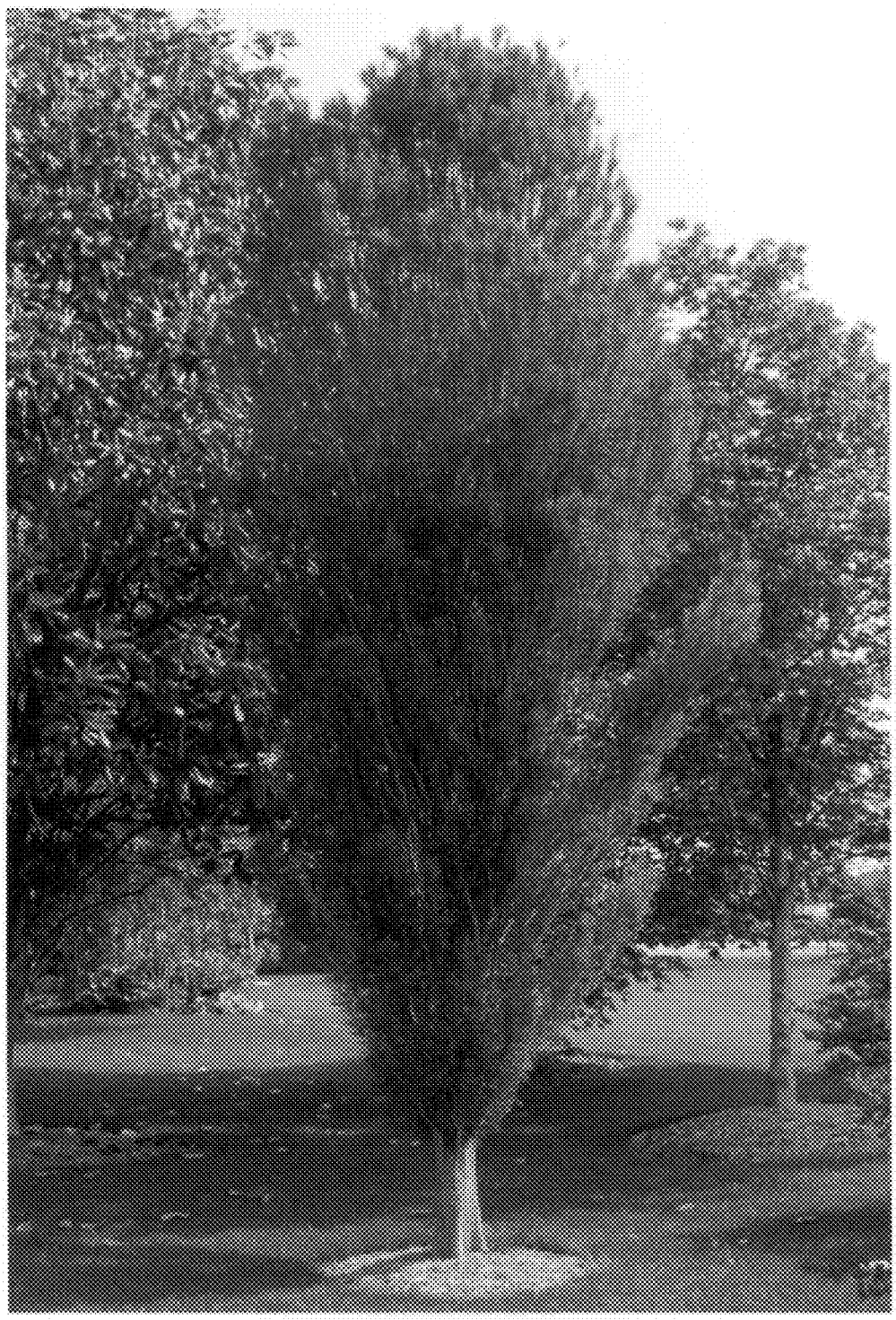
Figure 2:
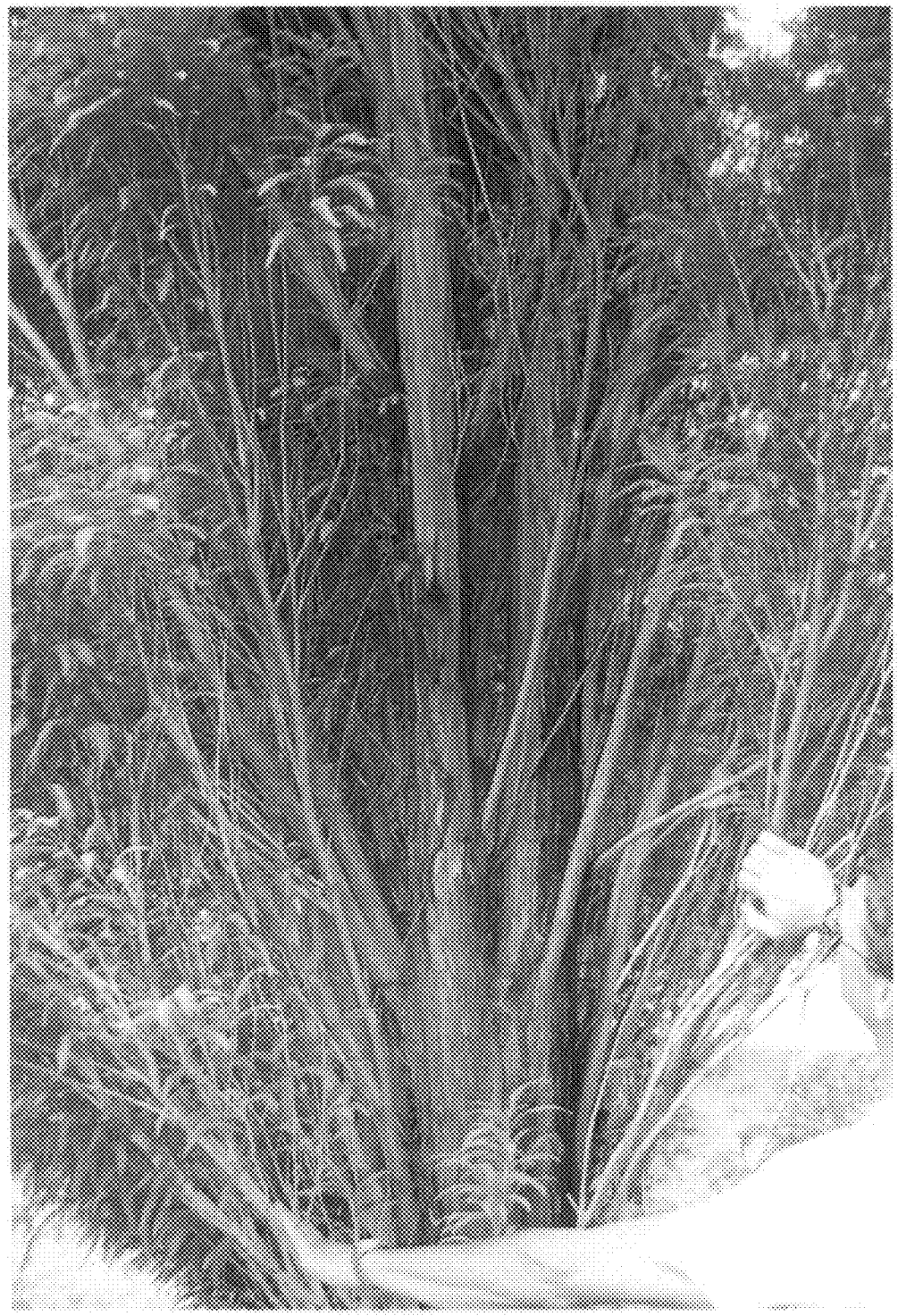

The photograph in FIG. 2 shows the ascending and dense branching habit of 'Skyward'.

Figure 3:
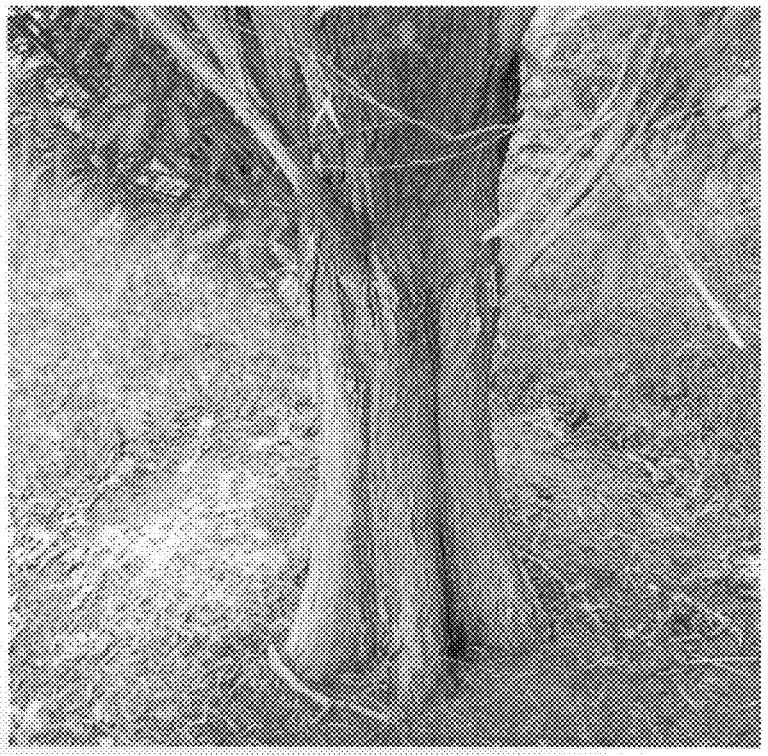

The photograph in FIG. 3 provides a view of the branches near the tree base of 'Skyward'.

Figure 4:
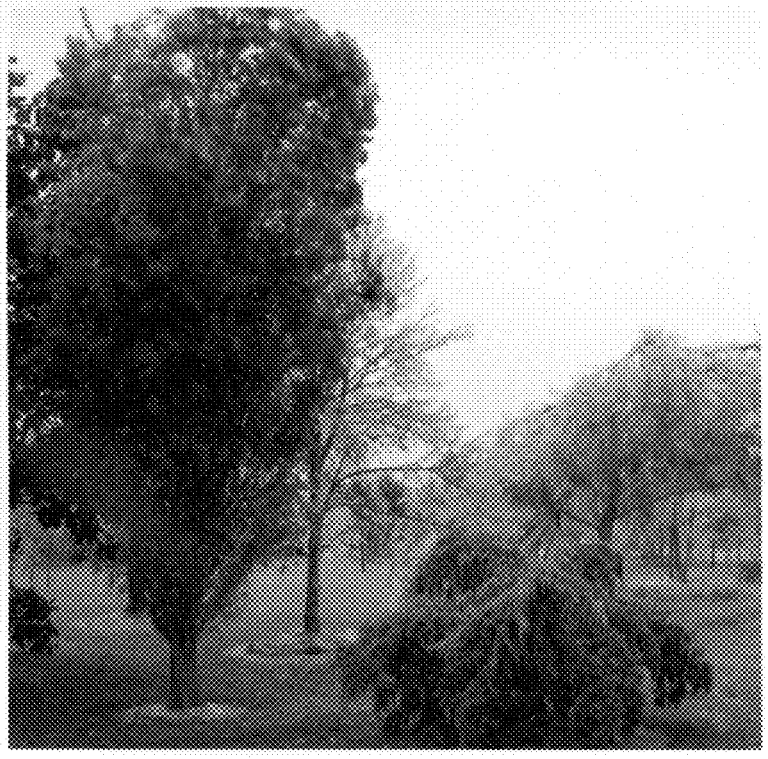

The photograph in FIG. 4 provides a view of 'Skyward' (left) in December after an ice storm and demonstrates it lack of damage. The Colors in the photograph may differ slightly from the color values cited in the detailed botanical description, which accurately describe the colors of the new *Taxodium.*

DETAILED BOTANICAL DESCRIPTION

The following is a detailed description of the new cultivar as observed on a tree grown in a field plot and garden for 20 years in Oklahoma, with detailed botanical data taken from plants about 2 years in age as grown outdoors in two-gallon containers in Oklahoma. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Deciduous, coniferous tree.

*Growth habit*.—Compact, upright, narrow (columnar), densely foliaged with a round apex, foliage extends to hear the base of the tree with about 4.0 cm of bare trunk at the base of a tree 7 m in height.

*Height and spread*.—Reaches about 7 m (23 feet) in height and 1.2 m (4 feet) in width in 20 years, 2 year-old plants grown in a 2-gallon container reach about 1 m in height and 50 cm in width.

*Cold hardiness*.—U.S.D.A. Zones 4 to 11.

*Diseases and pests*.—No susceptibility or resistance to diseases or pests has been observed.

*Growth rate*.—Moderate, grows about 30 to 60 cm (1 to 2 feet) per year.

*Propagation*.—Hardwood cutting, semi-hardwood cuttings, budding, and grafting.

*Root system*.—Tap-rooted, surface roots or cypress knees have not been observed when grown in moist soils.

Stem description:

*Shape*.—Rounded with base of main stem buttressed.

*Stem size*.—20 year-old plant: Main stem; about 24 cm in width measured 10 cm from base of tree and about 2 m in length becoming divided into several main branches about 4 m in length and 6 cm in width, lateral branches; an average of 1 m in length and 2 cm in width, 2 year-old plant; main stem; an average of 1 to 2 cm in diameter and 1 m in length; lateral branches; range from 4 to 7 mm in diameter and 12 to 48 cm in length.

*Stem surface*.—Young branches glabrous with a few scales, mature stems smooth and matte, striated bark towards the base.

*Stem color*.—Mature; blend of 172B and 172C suffused with 183A, older bark 200B, younger bark a blend of 199D and N200D, young stems; 167A towards base, 145A towards apex.

*Scales*.—Foliar, linear in shape, 0.1 to 1 cm in length, 1 mm in width, 145A on young stems, 167A on mature stems, deciduous.

*Branching*.—Numerous and densely branched with branches commencing close to base of tree, an average of 40 branches per main stem 1 m in length.

*Branch arrangement*.—Opposite to closely alternate.

*Branch aspect*.—Lateral stems ascending and held at about an average of a 25° angle from the main stem.

*Internode length*.—Ranges from 3 to 14 cm on 2 year-old plant.

Foliage description:

*Leaf arrangement*.—1 to 3 at each node closely alternate or opposite.

*Leaf shape*.—Narrowly lanceolate to linear.

*Leaf division*.—Pinnate, 50 to 150 pinnae per leaf.

*Leaf base*.—Cuneate.

*Leaf apex*.—Round with terminal pinnae approximately half the length of subapical pinnae.

*Leaf venation*.—Not visible.

*Pinnae margins*.—Entire.

*Pinnae size*.—An average of 1 cm in length and 2 mm in width.

*Leaf surface*.—Upper and lower surface; glabrous, smooth, glossy.

*Leaf color*.—Spring and summer; upper surface 137B, lower surface 138A, fall and winter; upper and lower surface changing to about 172A.

*Leaf fragrance*.—Subtle cedar and pine scented when crushed or brushed.

*Leaf size*.—An average of 5 to 20 cm in length and 2 cm in width.

*Leaf quantity*.—Numerous, about 1 leaf per cm in lateral branches.

*Leaf attachment*.—Sessile.

*Leaf aspect*.—Flat, feathery, arched downward.

Flower and fruit description: Flowers are typical of species; monoecious, male flowers minute and on panicles about 10 to 12 cm in length (4 to 5 inches), female flowers inconspicuous and comprised of several spirally arranged, overlapping scales, each scale bearing 2 ovules. The fruit is a globose cone, about 2.5 cm in diameter formed by the enlargement formed by the spirally pistillate flower scales, seed are two-winged, erect and borne under each scale. A detailed description of the flowers and cones was not possible on the plants available for data collection.

It is claimed:

1. A new and distinct cultivar of *Taxodium* tree named 'Skyward' as herein illustrated and described.

* * * * *